United States Patent
Duo et al.

(10) Patent No.: US 11,395,472 B2
(45) Date of Patent: Jul. 26, 2022

(54) TOMATO HYBRID T316108

(71) Applicant: Syngenta Crop Protection AG, Basel (CH)

(72) Inventors: Haoyang Duo, De Lier (NL); Marion Eble, Singapore (SG); Rob Schaareman, Nunhems (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/939,269

(22) Filed: Jul. 27, 2020

(65) Prior Publication Data

US 2022/0022412 A1    Jan. 27, 2022

(51) Int. Cl.
  *A01H 5/08*   (2018.01)
  *A01H 1/00*   (2006.01)
  *A01H 6/82*   (2018.01)

(52) U.S. Cl.
  CPC ............... *A01H 6/825* (2018.05); *A01H 5/08* (2013.01)

(58) Field of Classification Search
  None
  See application file for complete search history.

(56) References Cited

U.S. PATENT DOCUMENTS

2020/0029524 A1\* 1/2020 Silvertand ................ A01H 5/08

OTHER PUBLICATIONS

Certificate on the Grant of Community Plant Variety Rights—Sweetelle Tomato (Jan. 23, 2012).

\* cited by examiner

*Primary Examiner* — Phuong T Bui
(74) *Attorney, Agent, or Firm* — Katherine Seguin

(57) ABSTRACT

The invention provides tomato hybrid T316108 or line A11D13TEN000015 and plant parts, seed, and tissue culture therefrom. The invention also provides methods for producing a tomato plant by crossing the tomato plants of the invention with themselves or another tomato plant. The invention also provides tomato plants produced from such a crossing as well as plant parts, seed, and tissue culture therefrom.

22 Claims, No Drawings

TOMATO HYBRID T316108

FIELD OF THE INVENTION

This invention is in the field of tomato plants.

BACKGROUND OF THE INVENTION

Tomato is an important global crop. Several plant species associated with the family Solanaceae have been familiar to mankind since ancient times and are of great agricultural importance. The genus *Solanum* is a member of the Solanaceae family and includes the domesticated tomato *S. lycopersicum* (also known as *Lycopersicum esculentum*). Tomato is generally adapted to warm summer growing conditions but can also be grown in heated greenhouses under winter conditions. The introduction of hybrid tomato cultivars in the 1950s provided a magnitude of benefits including increased yield, better holding ability, adaptation to expanded growing seasons through the use of protected cultivation and improved disease resistances, which resulted in large-scale production of tomato as a commercial crop.

Tomato breeders make continual improvements in hybrid tomato yield, horticultural characteristics, and consumer quality traits. Thus, there is an ongoing need for improved tomato hybrid varieties and parental lines.

SUMMARY OF THE INVENTION

According to the invention, there is provided a novel hybrid tomato variety, designated Monile, also known as T316108, and parental tomato line AI1D13TEN000015.

The invention also encompasses the seeds of tomato hybrid T316108 and line AI1D13TEN000015, the plants of tomato hybrid T316108 and line AI1D13TEN000015, plant parts of the tomato hybrid T316108 and line AI1D13TEN000015 (including fruit, seed, gametes, rootstock, scions, shoots), methods of producing seed from tomato hybrid T316108 and line AI1D13TEN000015, and methods for producing a tomato plant by crossing the tomato hybrid T316108 or line AI1D13TEN000015 with itself or another tomato plant, methods for producing a tomato plant containing in its genetic material one or more transgenes, and the transgenic tomato plants produced by that method. The invention also relates to methods for producing other tomato plants derived from tomato hybrid T316108 or line AI1D13TEN000015 and to tomato plants, parts thereof and seed produced by the use of those methods. The present invention further relates to hybrid tomato seeds and plants (and parts thereof including fruit) produced by crossing tomato hybrid T316108 or line AI1D13TEN000015 with another tomato plant.

The invention further contemplates grafted tomato plants and methods of producing a grafted tomato plant, where tomato hybrid T316108 or line AI1D13TEN000015 can be used as either the rootstock or the scion.

In another aspect, the present invention provides regenerable cells for use in tissue culture of tomato hybrid T316108 and line AI1D13TEN000015. In embodiments, the tissue culture is capable of regenerating plants having all or essentially all of the physiological and morphological characteristics of the foregoing tomato plant and/or of regenerating plants having the same or substantially the same genotype as the foregoing tomato plant. In embodiments, the regenerated plant is a diploid plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, the present invention provides tomato plants regenerated from the tissue cultures of the invention.

As a further aspect, the invention provides a method of producing tomato seed, the method comprising crossing a plant of tomato hybrid T316108 or line AI1D13TEN000015 with itself or a second tomato plant, cultivating the plant to maturity, and allowing seed to form. Optionally, the method further comprises collecting the seed.

Another aspect of the invention provides methods for producing hybrids and other tomato plants derived from tomato hybrid T316108 or line AI1D13TEN000015. Tomato plants derived by the use of these methods are also part of the invention as well as plant parts, seed, gametes and tissue culture from such hybrid or derived tomato plants.

In representative embodiments, a tomato plant derived from tomato hybrid T316108 or line AI1D13TEN000015 comprises cells comprising at least one set of chromosomes derived from tomato hybrid T316108 or line AI1D13TEN000015. Those skilled in the art will appreciate that a plant derived from hybrid T316108 is also derived from parental line AI1D13TEN000015.

In embodiments, a tomato plant or population of tomato plants derived from tomato hybrid T316108 or line AI1D13TEN000015 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from tomato hybrid T316108 or line AI1D13TEN000015, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of tomato hybrid T316108 or line AI1D13TEN000015, respectively, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the tomato plant derived from tomato hybrid T316108 or line AI1D13TEN000015 is one, two, three, four, five or more breeding crosses removed from tomato hybrid T316108 or line AI1D13TEN000015, respectively.

In embodiments, a hybrid or derived plant from tomato hybrid T316108 or line AI1D13TEN000015 comprises a desired added trait(s). In representative embodiments, a tomato plant derived from tomato hybrid T316108 or line AI1D13TEN000015 comprises all of the morphological and physiological characteristics of tomato hybrid T316108 or line AI1D13TEN000015 (e.g., as described in Table 1), respectively, with the addition of the desired added trait(s). In embodiments, the tomato plant derived from tomato hybrid T316108 or line AI1D13TEN000015 comprises essentially all of the morphological and physiological characteristics of tomato hybrid T316108 or line AI1D13TEN000015 (e.g., as described in Table 1), respectively, with the addition of a desired added trait(s).

The invention also relates to methods for producing a tomato plant comprising in its genetic material one or more transgenes and to the transgenic tomato plant produced by those methods (and progeny tomato plants comprising the transgene). Also provided are plant parts, seed and tissue culture from such transgenic tomato plants, optionally wherein one or more cells in the plant part, seed, or tissue culture comprises the transgene. The transgene can be introduced via plant transformation and/or breeding techniques (e.g., once plant transformation of a precursor plant has been achieved, it can then be transferred to other plants via conventional breeding).

In another aspect, the present invention provides for single locus converted plants of tomato hybrid T316108 and line AI1D13TEN000015. Plant parts, seed, and tissue culture from such single locus converted plants are also contemplated by the present invention. The single locus may be a dominant or recessive allele. The single locus may be a naturally occurring tomato locus (e.g., introduced via traditional breeding or gene editing techniques), a transgene introduced into tomato through genetic engineering techniques (of the plant or a precursor thereof), or a non-naturally occurring locus (e.g., produced by mutagenesis or gene editing).

The invention further provides methods for developing tomato plants in a tomato plant breeding program using plant breeding techniques including, for example, recurrent selection, backcrossing, pedigree breeding, double haploid techniques, restriction fragment length polymorphism enhanced selection, genetic marker enhanced selection, gene editing and/or genetic transformation. Seeds, tomato plants, and parts thereof, produced by such breeding methods are also part of the invention.

The invention also provides methods of multiplication or propagation of tomato plants of the invention, which can be accomplished using any method known in the art, for example, via vegetative propagation and/or seed.

Additional aspects of the invention include harvested products and processed products from the tomato plants of the invention. A harvested product can be a whole plant or any plant part, as described herein. Thus, in some embodiments, a non-limiting example of a harvested product includes a seed, a fruit (e.g., including the flesh), a rootstock, a scion and/or a shoot.

In representative embodiments, a processed product includes, but is not limited to: cut, sliced, ground, dried, pureed, canned, jarred, washed, packaged, frozen, seeded, peeled and/or heated fruit or fruit flesh of the tomato plants of the invention, or any other part thereof, including puree, paste, sauce and salsa made from fruits or fruit flesh.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of tomato hybrid T316108 or line AI1D13TEN000015.

As a further aspect, the invention provides a plant of tomato hybrid T316108 or line AI1D13TEN000015.

As an additional aspect, the invention provides a tomato plant, or a part thereof, having all or essentially all of the physiological and morphological characteristics of a plant of tomato hybrid T316108 or line AI1D13TEN000015.

As another aspect, the invention provides fruit and fruit flesh of the tomato plants of the invention and processed products from the fruit or fruit flesh of the inventive tomato plants.

As still another aspect, the invention provides a method of producing tomato seed, the method comprising crossing a tomato plant of the invention with itself or a second tomato plant (e.g., crossing line AI1D13TEN000015 with another tomato line to produce a F1 hybrid seed (e.g., seed of T316108). In embodiments, the method is practiced to produce seed of line AI1D13TEN000015 (e.g., seed increase). The invention also provides seed produced by this method and plants, and parts thereof including fruit, produced by growing the seed.

As yet a further aspect, the invention provides a method for producing a seed of a tomato plant derived from tomato hybrid T316108 or line AI1D13TEN000015, the method comprising: (a) crossing a tomato plant of tomato hybrid T316108 or line AI1D13TEN000015 with a second tomato plant; and (b) allowing seed of a tomato plant derived from tomato hybrid T316108 or line AI1D13TEN000015 to form. In embodiments, the method further comprises: (c) growing a plant from the seed derived from tomato hybrid T316108 or line AI1D13TEN000015 of step (b); (d) selfing the plant of step (c) or crossing it to a second tomato plant to form additional tomato seed derived from tomato hybrid T316108 or line AI1D13TEN000015, and (e) optionally repeating steps (c) and (d) one or more times to generate further derived tomato seed from tomato hybrid T316108 or line AI1D13TEN000015, wherein in step (c) a plant is grown from the additional tomato seed of step (d) in place of growing a plant from the seed of step (b). In embodiments, the method comprises: (e) repeating steps (c) and (d) one or more times (e.g., three or more, four or more, five or more, six or more, one to three, one to five, one to six, one to seven, one to ten, one to five, three to six, three to seven, three to eight or three to ten times) to generate further derived tomato seed. As another option, the method can comprise cultivating the plant to maturity and collecting the seed. The invention also provides seed produced by these methods and tomato plants produced by growing the seed.

Still further, as another aspect, the invention provides a method of vegetatively propagating a plant of tomato hybrid T316108 or line AI1D13TEN000015, e.g., via shoot proliferation and then rooting in tissue culture. In a non-limiting example, the method comprises: (a) collecting tissue capable of being propagated from a plant of tomato hybrid T316108 or line AI1D13TEN000015; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods, as well as seed and fruits produced therefrom.

As a further aspect, the invention provides a method of producing a grafted tomato plant, wherein hybrid T316108 or line AI1D13TEN000015 is used as either the rootstock or the scion.

As an additional aspect, the invention provides a method of introducing a desired added trait into tomato hybrid T316108 or line AI1D13TEN000015, the method comprising: (a) crossing a first plant of tomato hybrid T316108 or line AI1D13TEN000015 with a second tomato plant that comprises a desired added trait to produce $F_1$ progeny; (b) selecting an $F_1$ progeny that comprises the desired trait; (c) crossing the selected $F_1$ progeny with tomato hybrid T316108 or line AI1D13TEN000015 to produce backcross progeny; and (d) selecting backcross progeny comprising the desired trait to produce a plant derived from tomato hybrid T316108 or line AI1D13TEN000015 comprising a desired trait.

In embodiments, the selected backcross progeny when tomato hybrid T316108 is used as the recurrent parent is characterized by 1, 2, 3, 4 or more of the characteristics of tomato hybrid T316108 as described herein, e.g., produces a strong generative plant type with good consistent setting, mature fruit with a shiny pink color and flesh, a small uniform fruit size, an oval plum shape, and/or an excellent taste. In embodiments, the selected backcross progeny when tomato line AI1D13TEN000015 is used as the recurrent parent is characterized by 1, 2, 3, 4 or more of the characteristics of tomato line AI1D13TEN000015 as described herein, e.g., produces a mature fruit with a yellow skin color, a uniform yellow mature fruit flesh and/or an oval plum shape. In embodiments, the selected progeny comprises all or essentially all the morphological and physiological characteristics of tomato hybrid T316108 or line AI1D13TEN000015 (e.g., a described in Table 1).

Optionally, the method further comprises: (e) repeating steps (c) and (d) one or more times (e.g., one to three, one to five, one to six, one to seven, one to ten, three to five, three to six, three to seven, three to eight or three to ten times) to produce a plant derived from tomato hybrid T316108 or line AI1D13TEN000015 comprising the desired trait, wherein in step (c) the selected backcross progeny produced in step (d) is used in place of the selected F1 progeny of step (b). In embodiments, the backcross of step (c) is repeated at least three, four, five, six or more times to produce an inbred line derived from tomato hybrid T316108 or line AI1D13TEN000015 and, optionally, the method further comprises crossing the derived inbred line with a different tomato line to produce an F1 hybrid progeny tomato plant derived from tomato hybrid T316108 or line AI1D13TEN000015.

In representative embodiments, the invention also provides a method of producing a plant of tomato hybrid T316108 or line AI1D13TEN000015 comprising a desired added trait, the method comprising introducing a transgene conferring the desired trait into a plant of tomato hybrid T316108 or line AI1D13TEN000015. The transgene can be introduced by transformation methods (e.g., genetic engineering) or traditional breeding techniques (e.g., once the transgene is introduced into a precursor plant).

The invention also provides tomato plants produced by the methods of the invention, wherein the tomato plant has the desired added trait as well as seed and fruits from such tomato plants. The invention also provides seed that produces the plants derived from hybrid T316108 or line AI1D13TEN000015 and comprising a desired added trait.

According to the foregoing methods, the desired added trait can be any suitable trait known in the art including without limitation: male sterility, male fertility, herbicide resistance, pest (e.g., insect and/or nematode) resistance, modified fatty acid metabolism, modified carbohydrate metabolism, disease resistance (e.g., against bacterial, fungal and/or viral disease), abiotic stress tolerance, enhanced nutritional quality (e.g., increased flavonoid content of the fruit), improved appearance (e.g., external fruit color and/or fruit flesh color), increased fruit sweetness, increased fruit flavor, improved fruit ripening, improved texture or taste, improved fruit yield, improved seed yield, improved seedling vigor, improved seed germination, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, transformed plants (e.g., using genetic engineering techniques), gene edited plants, single locus converted plants, hybrid plants and tomato plants derived from tomato hybrid T316108 are characterized by 1, 2, 3, 4 or more of the characteristics of tomato hybrid T316108 as described herein, e.g., produces a strong generative plant type with good consistent setting, mature fruit with a shiny pink color and flesh, a small uniform fruit size, an oval plum shape, and/or an excellent taste. In embodiments, transgenic plants, transformed plants (e.g., using genetic engineering techniques), gene edited plants, single locus converted plants, hybrid plants and tomato plants derived from tomato hybrid T316108 from tomato line AI1D13TEN000015 are characterized by 1, 2, 3, 4 or more of the characteristics of tomato line AI1D13TEN000015 as described herein, e.g., produces a mature fruit with a yellow skin color, a uniform yellow mature fruit flesh and/or an oval plum shape. In representative embodiments, transgenic plants, transformed plants, gene edited plants, hybrid plants and tomato plants derived from tomato hybrid T316108 or line AI1D13TEN000015 comprise essentially all of the morphological and physiological characteristics of tomato hybrid T316108 or line AI1D13TEN000015 (for example, as described in Table 1), respectively, or even all of the morphological and physiological characteristics of tomato hybrid T316108 or line AI1D13TEN000015, so that said plants are not significantly different for said traits than tomato hybrid T316108 or line AI1D13TEN000015, respectively, as determined at the 5% significance level when grown in the same environmental conditions; optionally, with the presence of one or more desired additional traits (e.g., as described above).

In one embodiment, the present invention discloses a method of producing seeds of tomato hybrid T316108 or line AI1D13TEN000015 comprising growing a plant of tomato hybrid T316108 or line AI1D13TEN000015; allowing pollination of said plants, for example, open-pollination of said plants in an isolated plot or field; and harvesting seeds from said plants. In one embodiment, the method further comprises washing and drying said seed.

The invention further provides a method of developing a tomato variety (e.g., a diploid tomato variety) in a tomato plant breeding program using plant breeding techniques, which include employing a tomato plant, or a part thereof, as a source of plant breeding material, the method comprising: (a) obtaining the tomato plant, or a part thereof, of hybrid T316108 or line AI1D13TEN000015 as a source of breeding material; and (b) applying plant breeding techniques.

The invention also encompasses plant parts, plant material, pollen, ovules, leaves, fruit and seed from the tomato plants of the invention. The invention also provides seed that produces the tomato plants of the invention. Also provided is a tissue culture of regenerable cells from the tomato plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are tomato plants regenerated from a tissue culture of the invention.

In still yet another aspect, the invention provides a method of determining a genetic characteristic of tomato hybrid T316108 or line AI1D13TEN000015 or a progeny thereof, e.g., a method of determining a genotype of tomato hybrid T316108 or line AI1D13TEN000015 or a progeny thereof using molecular genetic techniques. In embodiments, the method comprises detecting in the genome of a tomato hybrid T316108 or line AI1D13TEN000015 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel tomato hybrid T316108 and parental line AI1D13TEN000015. Among other characteristics, when grown under standard horticultural conditions (e.g., greenhouse), tomato hybrid T316108 is characterized by a mature fruit having a shiny pink skin color, a pink mature fruit flesh, oval plum shape, an average weight of about 10 grams, and an excellent taste. Among other characteristics, when grown under standard horticultural conditions (e.g., greenhouse), tomato line AI1D13TEN000015 is characterized by a mature fruit having a yellow skin color, a uniform yellow fruit flesh, oval plum shape, an average weight of about 9 to 10 grams, and an average diameter of about 2.8 cm.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions.

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Added trait": As used herein, a desired "added trait" or "additional trait" can be any trait that confers a desired characteristic to the plant, and may be introduced by any method known in the art, e.g., conventional breeding (for example, backcrossing), gene editing, mutagenesis, or genetic transformation techniques. Examples of added traits include without limitation: male sterility, male fertility, herbicide resistance, pest (e.g., insect and/or nematode) resistance, modified fatty acid metabolism, modified carbohydrate metabolism, disease resistance (e.g., against bacterial, fungal and/or viral disease), abiotic stress tolerance, enhanced nutritional quality (e.g., increased flavonoid content of the fruit), improved appearance (e.g., external fruit color and/or fruit flesh color), increased fruit sweetness, increased fruit flavor, improved fruit ripening, improved texture or taste, improved fruit yield, improved seed yield, improved seedling vigor, improved seed germination, industrial usage, gene editing machinery, or any combination thereof. The trait can be encoded by a DNA sequence (e.g., native tomato sequence, induced or naturally occurring mutation, edited native sequence, or a transgene) or can result from expression of a functional non-translated RNA (e.g., RNA interference).

"Allele". An allele is any of one or more alternative forms of a gene, all of which relate to a trait or characteristic. In a diploid cell or organism, the two alleles of a given gene occupy the corresponding locus on a pair of homologous chromosomes.

"Backcrossing". Backcrossing is a process in which a breeder repeatedly crosses hybrid progeny back to one of the parents (the "recurrent" parent), for example, a first generation hybrid $F_1$ with one of the parental genotype of the $F_1$ hybrid.

"Cotyledon". One of the first leaves of the embryo of a seed plant; typically one or more in monocotyledons, two in dicotyledons, and two or more in gymnosperms.

"Determinate": Determinate tomato plants tend to be compact and bushy in form, and the plant produces all of its fruit simultaneously within a short period of time (e.g., one to three weeks), and then fruit production stops.

"Double haploid line". A stable inbred line achieved by doubling the chromosomes of a haploid line, e.g., from anther culture. For example, some pollen grains (haploid) cultivated under specific conditions develop plantlets containing 1n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all of the physiological and morphological characteristics". A plant having "essentially all the physiological and morphological characteristics" (and similar phrases) means a plant having all of the desired physiological and morphological characteristics of hybrid T316108 or line AI1D13TEN000015, except for the characteristic(s) derived from a converted locus/loci (e.g., a single converted locus), for example, introduced via backcrossing to hybrid T316108 or line AI1D13TEN000015, a modified gene(s) resulting from genome editing techniques, an introduced transgene (i.e., introduced via genetic transformation techniques) or mutation, when both plants are grown under the same environmental conditions. In embodiments, a plant having "essentially all of the physiological and morphological characteristics" means a plant having all of the characteristics of the reference plant with the exception of five or fewer traits, 4 or fewer traits, 3 or fewer traits, 2 or fewer traits, or one trait. In embodiments, the plant comprising "essentially all of the physiological and morphological characteristics" of variety (e.g., for tomato hybrid T316108, a strong generative plant type with good consistent setting, mature fruit with a shiny pink color and flesh, a small uniform fruit size, and/or an oval plum shape or any other trait described herein, e.g., in Table 1; and for tomato line AI1D13TEN000015, a mature fruit with a yellow skin color, a uniform yellow mature fruit flesh and/or an oval plum shape or any other trait described herein, e.g., in Table 1).

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Gene editing": "Gene editing" (sometimes also called "genome editing") refers to the introduction of targeted modifications into genomic DNA using techniques employing, for example, meganucleases, zinc-finger nucleases, TALENs, and CRISPR/Cas9 systems. See, e.g., Gaj et al., ZFN, TALEN, and CRISPR/Cas-based methods for genome engineering. Trends in Biotechnology, 31:397-405 (2013).

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Indeterminate": Indeterminate tomato plants tend to be vine-like, and will grow and produce fruits throughout the season (e.g., until killed by frost).

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing. In representative embodiments, the plant part is a non-propagating plant part, for example, is not a seed.

"Quantitative Trait Locus". Quantitative Trait Locus (QTL) refers to a genetic locus that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A tomato plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus conversation". A single locus converted or conversion plant refers to a plant that is developed by plant breeding techniques (e.g., backcrossing), genome editing techniques, genetic transformation techniques and/or mutation techniques wherein essentially all of the desired morphological and physiological characteristics of a line are recovered in addition to the single locus introduced into the line via the plant breeding, genome editing, genetic transformation, or mutation techniques.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., an interfering RNA [RNAi]).

Botanical Description of Tomato Line AI1D13TEN000015 and Hybrid T316108.

When grown under standard horticultural conditions (e.g., in a greenhouse), the mature fruit of hybrid tomato T316108 is characterized by a number of traits including, without limitation: a mature fruit having a shiny pink skin color and flesh, oval plum shape, an average weight of about 10 grams, and an excellent taste.

When grown under standard horticultural conditions (e.g. in a greenhouse), the mature fruit of tomato line AI1D13TEN000015 is characterized by a number of traits including, without limitation: a mature fruit having a yellow skin color, a uniform yellow fruit flesh, oval plum shape, an average weight of about 9 to 10 grams, and an average diameter of about 2.8 cm.

Tomato line AI1D13TEN000015 has shown uniformity and stability within the limits of environmental influence. It has been self-pollinated for numerous generations with careful attention to uniformity of plant type. The variety has been increased with continued observation for uniformity. No variant traits have been observed or are expected in tomato line AI1D13TEN000015.

More detailed botanical descriptions of hybrid T316108 and line AI1D13TEN000015 are shown in Table 1 below.

TABLE 1

Variety Description Information (based on evaluation in a passive greenhouse).

Comparison of hybrid T316108 with a similar variety.

| Denomination of similar variety | Characteristic in which the similar variety is different | State of expression of similar variety | State of expression of candidate variety (T316108) |
|---|---|---|---|
| Sweetelle | Cluster shape | Long open clusters | Shorter compact clusters |
| Sweetelle | Plant vegetation | Open generative plant type | Vigorous vegetative plant type |
| Sweetelle | Fruit color | Red | Pink |

Additional information for tomato hybrid T316108.

| Characteristic | T316108 |
|---|---|
| Plant: growth type | Indeterminate |
| Time of maturity | Early-medium |
| Level of setting | Medium |
| Seedling: anthocyanin coloration of hypocotyl | Present |
| Stem: anthocyanin coloration of upper third | Very strong |
| Plant: height | Medium |
| Vigor of the plant | Medium-strong |
| Leaf: type of blade | Bipinnate |
| Leaf: intensity of green color | Medium |
| Peduncle: abscission layer | Present (jointed) |
| Fruit: size | Very small-small |
| Fruit: average weight in grams | 10 |
| Fruit: shape in longitudinal section | Obovate |
| Fruit: number of locules | Two or three |
| Fruit: green shoulder (before maturity) | Absent |
| Fruit: green stripes (before maturity) | Absent |
| Fruit: color at maturity | Pink |
| Fruit: color of flesh (at maturity) | Pink |
| Fruit: glossiness of skin | Shiny |
| Fruit: firmness | Medium-Firm |
| Fruit: ribbing at peduncle end | Weak |
| Fruit: shelf life | Medium - long |
| Fruit: shelf life in days | 16 |
| Homogeneity of size of the fruits | Uniform fruit size |
| Long shelf life gene(s) present? | Absent |
| Time of maturity (±comparable with the variety Sweetelle) | Early-medium |
| Resistances: | |
| *Fulvia fulva* group A | Susceptible |
| *Fulvia fulva* group B | Susceptible |
| *Fulvia fulva* group C | Susceptible |
| *Fulvia fulva* group D | Susceptible |
| *Fulvia fulva* group E | Susceptible |
| *Fusarium oxysporum* f. sp. *lycopersici* race 0 | Resistant |
| *Fusarium oxysporum* f. sp. *lycopersici* race 1 | Susceptible |
| *Fusarium oxysporum* f. sp. *radicis-lycopersici* | Intermediate resistant |
| *Verticillium dahliae* | Susceptible |

TABLE 1-continued

Variety Description Information (based on evaluation in a passive greenhouse).

| | |
|---|---|
| *Meloidogyne arenaria* | Intermediate resistant |
| *Meloidogyne incognita* | Intermediate resistant |
| *Meloidogyne javanica* | Intermediate resistant |
| Tobacco Mosaic Virus race 0 | Highly resistant |
| Tomato Mosaic Virus strain 0 | Highly resistant |
| Tomato Mosaic Virus strain 1 | Highly resistant |
| Tomato Mosaic Virus strain 1-2 | Highly resistant |
| Tomato Mosaic Virus strain 2 | Highly resistant |
| Tomato Spotted Wilt Virus | Susceptible |
| Tomato Yellow Leaf Curl Virus | Not tested |
| Sensitivity to silvering | Not tested |

Additional information for tomato inbread line, AI1D13TEN000015.

| Characteristic | AI1D13TEN000015 |
|---|---|
| Plant: growth type | Indeterminate |
| Time of flowering | Medium late |
| Time of maturity | Medium early |
| Seedling: anthocyanin coloration of hypocotyl | Present |
| Stem: pubescence (hairiness) | Sparsely hairy (scattered long hairs) |
| Stem: branching | Intermediate |
| Stem: branching at cotyledonary or $1^{st}$ leafy node | Absent |
| Stem: number of nodes between first inflorescence | Several (5-9) |
| Stem: number of nodes between early inflorescences ($1^{st}$-$2^{nd}$, $2^{nd}$-$3^{rd}$) | Few (1-4) |
| Stem: number of nodes between later developing inflorescences | Few (1-4) |
| Plant: height | 180 cm |
| Vigor of the plant | Medium-strong |
| Leaf: type of blade | Bipinnate |
| Leaflet: margins | Deeply toothed/cut toward base |
| Leaflet: marginal rolling or wiltiness | Strong |
| Leaflet: onset of leaflet rolling | Mid-season |
| Leaflet: surface of major leaflets | Rugose (bumpy/veiny) |
| Leaf: pubescence | Normal |
| Inflorescence: type ($2^{nd}$ and $3^{rd}$ truss) | Simple |
| Leafy or "running" inflorescences | Occasional |
| Average number of flowers in inflorescence | 18 |
| Flower: fasciation ($1^{st}$ flower of inflorescence) | Absent |
| Flower: Pubescence of style | Absent |
| Flower: color | Yellow |
| Flower: anthers | All fused in tube |
| Flower: calyx | Normal, lobes awl-shaped |
| Flower: calyx-lobes | Shorter than corolla |
| Time of flowering (greenhouse) in no. of days after sowing | 60 |
| Peduncle: abscission layer | Present (jointed) |
| Peduncle: length (from abscission layer to calyx) | 8 mm |
| Fruit: size | Very small-small |
| Fruit: size (average weight of 10 fruits) (g) | Very small (<100) |
| Fruit: average weight in grams | 11 |
| Fruit: typical shape | Plum or egg shape |
| Fruit length (cm) | 2.5 |
| Fruit: diameter (cm) | 2.8 |
| Fruit: shape in longitudinal section | Elliptic |
| Fruit: cross section | Round |
| Fruit: depression at peduncle end | Indented |
| Fruit: size peduncle scar | Small |
| Fruit: shape at blossom end | Flat |
| Fruit: size of core (in cross-section) | Absent |
| Fruit: thickness of pericarp | Thin |
| Fruit: epidermis | Normal |
| Fruit: epidermis color | Colorless |
| Fruit: epidermis texture | Tender |
| Fruit: number of locules | Two to three |
| Fruit: green shoulder (before maturity) | Present |
| Fruit: intensity of green color of shoulder | Light |
| Fruit: green stripes (before maturity) | Present |
| Fruit: intensity of green color before maturity | Light |
| Fruit: color at maturity | Yellow |
| Fruit: color of flesh (at maturity) | Uniform yellow |
| Fruit: surface | Smooth |

TABLE 1-continued

Variety Description Information (based on evaluation in a passive greenhouse).

| | |
|---|---|
| Fruit: locular gel color of table ripe fruit | Yellow |
| Fruit: point of detachment at harvest | At calyx attachment |
| Fruit: shelf life | Medium |
| Homogeneity of size of the fruits | Homogeneous |
| Long shelf life gene(s) present? | Absent |
| Fruit: shape of the pistil scar | Dot |
| Shape of the fruit in transverse section | Round |
| Resistances: | |
| *Fulvia fulva* group A | Susceptible |
| *Fulvia fulva* group B | Susceptible |
| *Fulvia fulva* group C | Susceptible |
| *Fulvia fulva* group D | Susceptible |
| *Fulvia fulva* group E | Susceptible |
| *Fusarium oxysporum* f. sp. *lycopersici* race 0 | Susceptible |
| *Fusarium oxysporum* f. sp. *lycopersici* race 1 | Susceptible |
| *Fusarium oxysporum* f. sp. *radices-lycopersici* | Susceptible |
| *Verticillium albo-atrum* | Susceptible |
| *Verticillium dahlia* | Susceptible |
| *Meloidogyne arenaria* | Intermediately resistant |
| *Meloidogyne incognita* | Intermediately resistant |
| *Meloidogyne javanica* | Intermediately resistant |
| Tobacco Mosaic Virus race 0 | Highly resistant |
| Tomato Mosaic Virus strain 0 | Highly resistant |
| Tomato Mosaic Virus strain 1 | Highly resistant |
| Tomato Mosaic Virus strain 1-2 | Highly resistant |
| Tomato Mosaic Virus strain 2 | Highly resistant |
| Tomato Spotted Wilt Virus | Susceptible |
| Tomato Yellow Leaf Curl Virus | Susceptible |
| Sensitivity to silvering | Not tested |

Tissue Culture.

In embodiments, tomato plants can be propagated by tissue culture and regeneration. Tissue culture of various plant tissues and regeneration of plants therefrom is well known. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a high rate of success. Thus, another aspect of this invention is to provide cells which upon growth and differentiation produce tomato plants having desired characteristics of tomato hybrid T316108 or line AI1D13TEN000015. Optionally, tomato plants can be regenerated from the tissue culture of the invention comprising all or essentially all of the physiological and morphological characteristics of tomato hybrid T316108 or line AI1D13TEN000015.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a tomato plant by crossing a first parent tomato plant with a second parent tomato plant wherein the first and/or second parent tomato plant is a plant of tomato hybrid T316108 or line AI1D13TEN000015. Thus, any of the following exemplary methods using tomato hybrid T316108 or line AI1D13TEN000015 are part of this invention: selfing, backcrosses, hybrid production, crosses to populations, double haploid production, and the like. All plants produced using tomato hybrid T316108 or line AI1D13TEN000015 as at least one parent are within the scope of this invention, including those developed from tomato plants derived from tomato hybrid T316108 or line AI1D13TEN000015. Advantageously, tomato hybrid T316108 or line AI1D13TEN000015 can be used in crosses with other, different, tomato plants (e.g., inbred lines) to produce first generation ($F_1$) tomato hybrid seeds and plants with desirable characteristics. The tomato plants of the invention can also be used for transformation where exogenous transgenes are introduced and expressed by the plants of the invention or for introduction of genetic changes by gene editing or mutagenesis. Genetic variants created either through traditional breeding methods, gene editing, mutagenesis or transformation of the cultivars of the invention by any of a number of protocols known to those of skill in the art are intended to be within the scope of this invention.

The following describes exemplary breeding methods that may be used with tomato hybrid T316108 or line AI1D13TEN000015 in the development of further tomato plants. One such embodiment is a method for developing tomato hybrid T316108 or line AI1D13TEN000015 progeny tomato plants (e.g., a diploid progeny tomato plant) in a tomato plant breeding program comprising: obtaining a plant, or a part thereof, of tomato hybrid T316108 or line AI1D13TEN000015, utilizing said plant or plant part as a source of breeding material, and selecting a tomato hybrid T316108 or line AI1D13TEN000015 progeny plant with some, all or essentially all morphological and/or physiological characteristics of tomato hybrid T316108 or line AI1D13TEN000015 (see, e.g., Table 1), respectively, optionally with the use of molecular markers. In representative embodiments, a progeny plant of tomato hybrid T316108 has at least 1, 2, 3, 4 or more of the morphological and physiological characteristics of tomato hybrid T316108 (for example, produces a mature fruit having a shiny pink skin color, a pink mature fruit flesh, oval plum shape, an average weight of about 10 grams, and an excellent taste). In embodiments, a progeny plant of tomato line AI1D13TEN000015 has at least 1, 2, 3, 4 or more of the characteristics of tomato line AI1D13TEN000015 (for example, produces a mature fruit having a yellow skin color, a uniform yellow fruit flesh, oval plum shape, an average weight of about 9 to 10 grams, and an average diameter of about 2.8 cm). In embodiments, a progeny plant of tomato hybrid T316108 or tomato line AI1D13TEN000015 comprises essentially all or even all of the morphological and physiological characteristics of tomato hybrid T316108 or line AI1D13TEN000015, respectively so that said progeny tomato plant is not significantly different for said traits than tomato hybrid T316108 or line AI1D13TEN000015, respectively, as determined at the 5% significance level when grown in the same environmental conditions; optionally, with the presence of one or more desired added traits. Breeding steps that may be used in the breeding program include pedigree breeding, backcrossing, mutation breeding, recurrent selection and/or double haploid production. In conjunction with these steps, techniques such as RFLP-enhanced selection, genetic marker enhanced selection (for example, SSR markers) and/or and the making of double haploids may be utilized.

Another representative method involves producing a population of tomato hybrid T316108 or line AI1D13TEN000015 progeny plants (e.g., diploid progeny plants), comprising crossing tomato hybrid T316108 or line AI1D13TEN000015 with another tomato plant, thereby producing a population of tomato plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from tomato hybrid T316108 or line AI1D13TEN000015, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of tomato hybrid T316108 or line AI1D13TEN000015. One embodiment of this invention is the tomato plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from tomato hybrid T316108 or line AI1D13TEN000015, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology.

One of ordinary skill in the art of plant breeding would know how to evaluate the traits of two plants to determine if there is or is not significant difference between the two traits expressed by those plants. For example, see Fehr and Walt, Principles of Cultivar Development, pp. 261-286 (1987). Thus, in embodiments, the invention includes tomato hybrid T316108 progeny tomato plants characterized by e.g., 1, 2, 3, 4 or more characteristics of tomato hybrid T316108 as described herein, e.g., produces a mature fruit having a shiny pink skin color, a pink mature fruit flesh, oval plum shape, an average weight of about 10 grams, and an excellent taste. In embodiments, the invention includes tomato line AI1D13TEN000015 progeny tomato plants characterized by 1, 2, 3, 4 or more of the characteristics of tomato line AI1D13TEN000015 as described herein, e.g., produces a mature fruit having a yellow skin color, a uniform yellow fruit flesh, oval plum shape, an average weight of about 9 to 10 grams, and an average diameter of about 2.8 cm. In embodiments, the selected progeny comprises all or essentially all the morphological and physiological characteristics of tomato hybrid T316108 or line AI1D13TEN000015 (e.g., a described in Table 1). In embodiments, the invention encompasses progeny plants having a combination of at least 2, 3, 4, 5, 6, 7, 8, 9, 10 or more of the characteristics as described herein for tomato hybrid T316108 or line AI1D13TEN000015 (see, e.g., Table 1), so that said progeny tomato plant is not significantly different for said traits than tomato hybrid T316108 or line AI1D13TEN000015, respectively, as determined at the 5% significance level when grown in the same environmental conditions. Using techniques described herein and those known in the art, molecular markers may be used to identify said progeny plant as progeny of tomato hybrid T316108 or line AI1D13TEN000015. Mean trait values may be used to determine whether trait differences are significant, and optionally the traits are measured on plants grown under the same environmental conditions.

Progeny of tomato hybrid T316108 or line AI1D13TEN000015 may also be characterized through their filial relationship with tomato hybrid T316108 or line AI1D13TEN000015, as for example, being within a certain number of breeding crosses of tomato hybrid T316108 or line AI1D13TEN000015. A breeding cross is a cross made to introduce new genetics into the progeny, and is distinguished from a cross, such as a self or a sib cross or a backcross to either tomato hybrid T316108 or line AI1D13TEN000015 as a recurrent parent, made to select among existing genetic alleles. The lower the number of breeding crosses in the pedigree, the closer the relationship between tomato hybrid T316108 or line AI1D13TEN000015 and its progeny. For example, progeny produced by the methods described herein may be within 1, 2, 3, 4, 5 or more breeding crosses of tomato hybrid T316108 or line AI1D13TEN000015. Those skilled in the art will appreciate that a progeny of hybrid T316108 is also a progeny of parental line AI1D13TEN000015, just the generational relationship is different.

In representative embodiments, a tomato plant derived from tomato hybrid T316108 or line AI1D13TEN000015 comprises cells comprising at least one set of chromosomes derived from tomato hybrid T316108 or line AI1D13TEN000015. In embodiments, the tomato plant or population of tomato plants derived from tomato hybrid T316108 or line AI1D13TEN000015 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from tomato hybrid T316108 or line AI1D13TEN000015, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of tomato hybrid T316108 or line AI1D13TEN000015, and optionally may be the result of one or more of selfing, sibbing, backcrossing and/or double haploid techniques in any combination. In embodiments, the tomato plant derived from tomato hybrid T316108 or line AI1D13TEN000015 is one, two, three, four, five or more breeding crosses removed from tomato hybrid T316108 or line AI1D13TEN000015.

In representative embodiments, a plant derived from tomato hybrid T316108 or line AI1D13TEN000015 is a double haploid plant, a hybrid plant, an inbred plant, and/or a diploid plant.

In embodiments, a derived plant from tomato hybrid T316108 or line AI1D13TEN000015 comprises a desired added trait. In representative embodiments, a tomato plant derived from tomato hybrid T316108 or line AI1D13TEN000015 comprises all of the morphological and physiological characteristics of tomato hybrid T316108 or line AI1D13TEN000015 (e.g., as described in Table 1). In embodiments, the tomato plant derived from tomato hybrid T316108 or line AI1D13TEN000015 comprises essentially all of the morphological and physiological characteristics of tomato hybrid T316108 or line AI1D13TEN000015 (e.g., as described in Table 1), with the addition of a desired added trait.

Those skilled in the art will appreciate that traits can be introduced into tomato hybrid T316108 or line AI1D13TEN000015 by any method known in the art, e.g., plant transformation methods, conventional breeding, gene editing and/or natural or induced mutations.

Further Embodiments of the Invention

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of tomato plants disclosed herein.

Genetic engineering techniques can be used (alone or in combination with breeding methods) to introduce one or more desired added traits into plant, for example, tomato hybrid T316108 or line AI1D13TEN000015 or progeny or tomato plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed tomato plants using transformation methods as described herein to incorporate transgenes into the genetic material of the tomato plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a tomato plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for gene editing techniques.

Any transgene, including those exemplified above, can be introduced into the tomato plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *Agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic tomato line. The transgenic tomato line can then be crossed with another (non-transgenic or transgenic) line in order to produce a new transgenic tomato line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Locus Conversions.

When the term "plant" is used in the context of the present invention, this term also includes any locus conversions of that plant or variety. The term "locus converted plant" as used herein refers to those plants that are developed, for example, by backcrossing, genome editing, genetic transformation and/or mutation, wherein essentially all of the desired morphological and physiological characteristics of a variety (e.g., for tomato hybrid T316108, a mature fruit having a shiny pink color, a pink mature fruit flesh, oval plum shape, an average weight of about 10 grams or any other trait described herein, e.g., in Table 1; and for tomato line AI1D13TEN000015, a mature fruit having a yellow skin color, a uniform yellow fruit flesh, oval plum shape, an average weight of about 9 to 10 grams or any other trait described herein, e.g., in Table 1) are recovered in addition to the one or more genes introduced into the variety.

To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Genetic Analysis of Tomato Hybrid T316108 or Line AI1D13TEN000015.

The invention further provides a method of determining a genetic characteristic of tomato hybrid T316108 or line AI1D13TEN000015 or a progeny thereof, e.g., a method of determining a genotype of tomato hybrid T316108 or line AI1D13TEN000015 or a progeny thereof. In embodiments, the method comprises detecting in the genome of a tomato hybrid T316108 or line AI1D13TEN000015 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

Although the present invention has been described with reference to specific details of certain embodiments thereof, it is not intended that such details should be regarded as limitations upon the scope of the claimed invention except as and to the extent that they are included in the accompanying claims.

DEPOSIT INFORMATION

Applicants have made a deposit of at least 2500 seeds of and tomato hybrid T316108 with American Type Culture Collection (ATCC), 10801 University Boulevard, Manassas, Va., 20110-2209 U.S.A. under ATCC Accession No. PTA-126904 on Nov. 24, 2020 under the provisions of the Budapest Treaty. This deposit of tomato hybrid T316108 will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to these deposits will be made available during the pendency of this application to the Commissioner upon request. All restrictions on the availability of the deposited material from ATCC to the public will be irrevocably and without restriction removed upon granting of the patent. Applicants impose no restrictions on the availability of the deposited material from ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single locus modifications and mutations, somaclonal variants, variant individuals selected from large populations of the plants of the instant cultivars and the like may be practiced within the scope of the invention.

What is claimed is:

1. A seed that produces tomato hybrid T316108, a representative sample of seed having been deposited under ATCC Accession No. PTA-126904.

2. A plant of tomato hybrid T316108 produced from the seed of claim 1.

3. A tomato plant, or a part thereof, having all the physiological and morphological characteristics of the tomato plant of claim 2.

4. A seed that produces the plant of claim 3.

5. A plant part of the plant of claim 2, wherein said plant part is a leaf, a fruit, a shoot, pollen, an ovule, an anther, a root, a rootstock, a scion, or a cell.

6. A tissue culture of regenerable cells of the tomato plant of claim 2.

7. A tomato plant regenerated from the tissue culture of claim 6 or a selfed progeny thereof, wherein said tomato plant comprises all of the physiological and morphological characteristics of tomato hybrid T316108.

8. A method of producing tomato seed, the method comprising crossing the plant of claim 2 with itself or a second tomato plant and harvesting the resulting seed.

9. A grafted tomato plant comprising a rootstock and a scion, wherein the plant of claim 2 is used as the scion and the rootstock is from a different tomato plant.

10. A method of producing a grafted tomato plant, the method comprising:
  (a) providing a scion from the plant of claim 2; and
  (b) grafting the scion to a rootstock from a different tomato plant.

11. A method of developing a tomato line in a tomato plant breeding program using plant breeding techniques, which include employing a tomato plant, or a part thereof, as a source of plant breeding material, the method comprising:
  (a) obtaining the tomato plant, or part thereof, of claim 2 as a source of breeding material; and (b) applying plant breeding techniques to said tomato plant or part thereof.

12. A method for producing a seed of a tomato plant derived from the tomato hybrid T316108, the method comprising:
   (a) crossing the plant of claim 2 with a different tomato plant;
   (b) allowing seed to form;
   (c) growing a plant from the seed of step (b) to produce a plant derived from tomato hybrid T316108;
   (d) selfing the plant of step (c) or crossing it to a second tomato plant to form additional tomato seed derived from tomato hybrid T316108; and
   (e) optionally repeating steps (c) and (d) one or more times to generate further derived tomato seed from tomato hybrid T316108, wherein in step (c) a plant is grown from the additional tomato seed of step (d) in place of growing a plant from the seed of step (b).

13. A method of vegetatively propagating tomato hybrid T316108, the method comprising:
   (a) collecting tissue capable of being propagated from the plant of claim 2;
   (b) cultivating the tissue to obtain proliferated shoots;
   (c) rooting the proliferated shoots to obtain rooted plantlets; and
   (d) optionally, growing plants from the rooted plantlets.

14. A tomato plantlet or plant obtained by the method of claim 13, wherein the tomato plantlet or plant comprises all of the physiological and morphological characteristics of tomato hybrid T316108.

15. A method of producing a plant of tomato hybrid T316108 comprising a desired added trait, the method comprising introducing a transgene conferring the desired trait into the plant of claim 2.

16. A tomato plant produced by the method of claim 15, wherein the tomato plant comprises the transgene conferring the desired trait and otherwise comprises all of the morphological and physiological characteristics of tomato hybrid T316108.

17. A seed that produces the plant of claim 16.

18. A method for producing a tomato seed, the method comprising selfing the plant of claim 2, which is tomato hybrid T316108, for one or more generations and allowing seed to form.

19. A method of producing a tomato fruit, the method comprising:
   (a) growing the tomato plant according to claim 2 to produce a tomato fruit; and
   (b) harvesting the tomato fruit.

20. A method of producing a processed tomato product, the method comprising:
   (a) obtaining a fruit of the plant of claim 2; and
   (b) processing said fruit to produce a processed product.

21. A method of determining a genotype of tomato hybrid T316108, the method comprising:
   (a) obtaining a sample of nucleic acids from the plant of claim 2; and
   (b) detecting a polymorphism in the nucleic acid sample using molecular biology techniques thereby determining the genotype of tomato hybrid T316108.

22. A plant of tomato hybrid T316108, or a seed that produces tomato hybrid T316108, said seed deposited as ATCC Accession No. PTA-126904.

* * * * *